United States Patent [19]

King et al.

[11] Patent Number: 5,620,992

[45] Date of Patent: Apr. 15, 1997

[54] HETEROARYL COMPOUNDS USED AS PHARMACEUTICALS

[75] Inventors: Francis D. King; Laramie M. Gaster, both of Bishop's Stortford; Keith R. Mulholland, Harlow, all of England

[73] Assignee: SmithKline Beecham plc, Brentford, England

[21] Appl. No.: 397,229

[22] PCT Filed: Sep. 7, 1993

[86] PCT No.: PCT/GB93/01895

§ 371 Date: Mar. 10, 1995

§ 102(e) Date: Mar. 10, 1995

[87] PCT Pub. No.: WO94/03654

PCT Pub. Date: Mar. 17, 1994

[30] Foreign Application Priority Data

Sep. 10, 1992 [GB] United Kingdom .................... 9219163

[51] Int. Cl.$^6$ ....................... A61K 31/445; C07D 405/12
[52] U.S. Cl. .......................... 514/321; 514/306; 546/138; 546/197
[58] Field of Search ..................... 546/138, 197; 514/306, 321; 540/596; 548/337.1, 950

[56] References Cited

U.S. PATENT DOCUMENTS

| 4,186,135 | 1/1980 | Thominet et al. | 514/321 |
| 4,268,512 | 5/1981 | Thominet et al. | 514/321 |
| 5,374,637 | 12/1994 | Van Daele et al. | 514/320 |

FOREIGN PATENT DOCUMENTS

| 0407137A2 | 1/1991 | European Pat. Off. . |
| 2176785A | 1/1987 | United Kingdom . |
| 10494 | 6/1992 | WIPO . |
| WO93/05038 | 3/1993 | WIPO . |

Primary Examiner—Ceila Chang
Attorney, Agent, or Firm—Charles M. Kinzig; Stephen Venetianer; Edward T. Lentz

[57] ABSTRACT

A compound of formula (I)

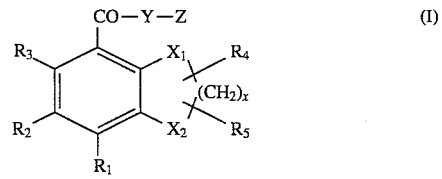

wherein $R_1$, $R_2$, $R_3$, $R_4$, $R_5$, $X_1$, $X_2$, x, Y and Z are as defined in the specification are useful in the treatment or prophylaxis of gastrointestinal disorders, cardiovascular disorders and CNS disorders.

19 Claims, No Drawings

HETEROARYL COMPOUNDS USED AS PHARMACEUTICALS

This application is a 371 of PCT/GB93/01895 filed Sep. 7, 1993.

This invention relates to the use of compounds as 5-HT$_4$ receptor antagonists in the treatment of gastrointestinal disorders, CNS disorders and/or cardiovascular disorders, and to certain novel compounds having 5-HT$_4$ receptor antagonist activity.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205–930, which is also a 5-HT$_3$ receptor antagonist, acts as an antagonist at this receptor.

Some 5-HT$_3$ receptor antagonists have been disclosed as of potential use in the treatment of certain aspects of irritable bowel syndrome (see EP-A-189002 (Sandoz Limited) and EP-A-201165 (Beecham Group p.l.c)).

5-HT$_3$ receptor interactions which are of potential use in the treatment of IBS are those associated either with the visceral pain and abnormal perception of sensation aspects of this disease, or they are related to the ability of some 5-HT$_3$ receptor antagonists to cause constipation in volunteers.

Some 5-HT$_3$ receptor antagonists have been disclosed as of potential use in the treatment of gastrointestinal disorders associated with upper gut motility [see EP-A-226266 (Glaxo Group Ltd.) and EP-A-189002 (Sandoz Limited)]. 5-HT$_3$ receptor antagonists are also well known antiemetics, such as ondansetron, granisetron and tropisetron (see Drugs of the Future 1989, 14 (9) p.875- F. D. King and G. J. Sanger).

WO 91/16045 (SmithKline and French Laboratories Limited) describes the use of cardiac 5-HT$_4$ receptor antagonists in the treatment of atrial arrhythmias and stroke.

EP-A-36269 (Beecham Group p.l.c.) describes a group of compounds of potential use in the treatment of gastrointestinal motility disorders. WO 92/10494 (Beecham Group p.l.c.) describes 5-HT$_3$ receptor antagonists derived from a benzoic acid nucleus 2,3 disubstituted by alkylenedioxy. WO 93/05038 (SmithKline Beecham p.l.c.) describes 5-HT$_4$ receptor antagonists derived from a benzoic acid nucleus.

EP-A-501322 (Glaxo Group Limited) describes indole derivatives having 5-HT$_4$ antagonist activity.

It has now been discovered that certain novel compounds have 5-HT$_4$ receptor antagonist properties;

When used herein, 'treatment' includes prophylaxis as appropriate.

Accordingly, the present invention provides a compound of formula (I) and pharmaceutically acceptable salts thereof, and the use of a compound of formula (I) or a pharmaceutically acceptable salt thereof:

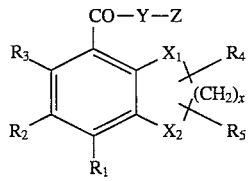

in which $X_1$—$(CH_2)_x$—$X_2$ forms a 5–7 membered ring wherein:

$X_1$ is O or S;

$X_2$ is O, S, NR or NRCO wherein R is hydrogen or $C_{1-6}$ alkyl;

x is 1, 2 or 3;

$R_1$ is hydrogen, amino, halo, $C_{1-6}$ alkyl, hydroxy or $C_{1-6}$ alkoxy;

$R_2$ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkoxy or amino;

$R_4$ and $R_5$ are independently hydrogen or $C_{1-6}$ alkyl;

Y is O or NH;

Z is of sub-formula (a):

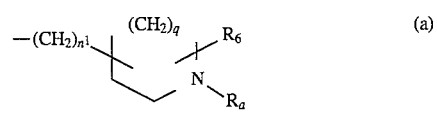

wherein

—$(CH_2)_{n^1}$ is attached at carbon; and $n^1$ is 0, 1, 2, 3 or 4;

q is 0, 1, 2 or 3;

$R_a$ is $(CH_2)_{n^2}$-$R_7$ wherein $n^2$ is 2 or 3 and $R_7$ is selected from cyano, hydroxyl, $C_{1-6}$ alkoxy, phenoxy, $C(O)C_{1-6}$ alkyl, $COC_6H_5$, —$CONR_8R_9$, $NR_8COR_9$, $SO_2NR_8R_9$ or $NR_8SO_2R_9$ wherein $R_8$ and $R_9$ are hydrogen or $C_{1-6}$ alkyl; and $R_6$ is hydrogen or $C_{1-6}$ alkyl;

or a compound of formula (I) wherein the CO—Y linkage is replaced by a heterocyclic bioisostere;

in the manufacture of a medicament for use as a 5-HT$_4$ receptor antagonist.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo, preferably chloro.

A suitable bioisostere for the amide or ester linkage containing Y in formula (I), is of formula:

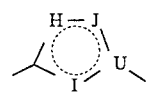

wherein the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of the bioisostere are as described for X, Y and Z in EP-A-328200 (Merck Sharp & Dohme Ltd.), such as an oxadiazole moiety.

Suitable examples of the $X_1$—$(CH_2)_x$—$X_2$ moiety include O—$(CH_2)_2$—O, O—$(CH_2)_3$—O, O—$CH_2$—O, O—$(CH_2)_2$—NR, O—$(CH_2)_2$—S or O—$CH_2$—CONR, wherein any of the methylene linkages are optionally mono- or di-substituted by $C_{1-6}$ alkyl groups, such as methyl. Preferably $X_1$—$(CH_2)_2$—$X_2$ is O—$(CH_2)_2$—O.

$R_1$ is preferably hydrogen or amino.

$R_2$ is preferably hydrogen or halo.

$R_3$ is preferably hydrogen or halo.

$R_4$ and $R_5$ are often hydrogen. When $R_4/R_5$ is $C_{1-6}$ alkyl, it is often methyl. In particular $R_4$ and $R_5$ are methyl such that the disubstituent containing $X_1$ and $X_2$ is O—C(CH$_3$)$_2$—O.

Y may be O or NH, in particular.

$n^1$ is preferably 1 and the azacycle is preferably attached at a 4-position carbon atom, when q is 2.

Values of $R_a$ are described for $(CH_2)_nR^4$ in formula (I), in relation to (Ia), preferred classes therein and the specific examples of EP-A-501322.

Other values of Z of interest are described with reference to the Examples, in particular, wherein $R_a$ is hydroxypropyl and/or wherein the 4-piperidinyl group is replaced by 3-pyrrolidinyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) wherein CO-Y is an ester or amide linkage are prepared by conventional coupling of the Z moiety with the appropriate acid. Suitable methods are as described in GB 2125398 A (Sandoz Limited), GB 1593146A, EP-A-36269, EP-A-289170 and WO 92/05174 (Beecham Group p.l.c.). When CO-Y is replaced by a heterocyclic bioisostere, suitable methods are described in EP-A-328200 (Merck Sharp & Dohme Limited). Reference is also made to EP-A-501322 (Glaxo Group Limited).

The invention also comprises a process for preparing the novel compounds of formula (I) which comprises reacting an appropriate benzoic acid derivative with an appropriate alcohol or amine. A process comprises reacting a benzoic acid derivative wherein the aromatic substituents are as required in the end compound of formula (I), or substituents convertible thereto, with an alcohol or amine containing Z or a group convertible thereto, and thereafter if necessary, convening the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination, and/or elaboration of a 2,3-disubstituted benzoic acid with ethylene glycol to form the benzodioxan. Any elaboration of the benzo-fused $X_1$—$(CH_2)_x$—$X_2$ containing moiety is, however, usually carried out prior to ester or amide coupling.

Suitable examples of conversions in the Z containing moiety include conventional modifications of the N-substituent by substitution and/or deprotection or, in the case of a 2-, 3- or 4- substituted piperidinyl desired end compound, reduction of an appropriate pyridyl derivative.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective mount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Example illustrates the preparation of compounds of formula (I), the following Descriptions relate to the preparation of intermediates.

It will be appreciated that any compound prepared wherein Y is O may be provided as the corresponding compound wherein Y is NH.

EXAMPLES

| Compound | $R_a$ |
|---|---|
| E1 | $(CH_2)_3OH$ |
| E2 | $(CH_2)_2CN$ |
| E3 | $(CH_2)_2COCH_3$ |
| E4 | $(CH_2)_2NHSO_2CH_3$ |
| E5 | $(CH_2)_2NHCOCH_3$ |

The corresponding compounds to those of the Examples but wherein $R_a$ is $(CH_2)_2SO_2NHCH_3$ or $(CH_2)_2CONH_2$ (wherein Y is O or NH) are also prepared as described herein and with reference to EP-A-501322 (Glaxo Group Limited).

EXAMPLE 1

[1-(3-Hydroxypropyl)-4-piperidinyl]methyl 8-amino-7-chloro-1,4-benzodioxan-5-carboxylate hydrochloride (E1)

To a solution of 4-piperidinylmethyl 8-amino-7-chloro-1,4-benzodioxan-5-carboxylate (100mg) and triethylamine (60 μl) in acetone (15 ml) was added 3-bromo-1-propanol (30 μl). The reaction mixture was heated under reflux overnight. The reaction mixture was cooled to room temperature and the solvent concentrated in vacuo. The residue was chromatographed on silica using chloroform and ethanol as the eluant to afford pure product (73 mg). Treatment with ethereal HCl afforded title compound. $^1$H NMR 250 MHz (CD$_3$OD) δ: 7.44(s,1H), 4.35(s,4H), 4.18(d,2H), 3.65–3.71(m,4H), 3.24(t,2H), 3.04(t,2H), 1.92–2.16(m,5H), 1.59–1.80(m,2H)

EXAMPLE 2

[1-(2-Cyanoethyl)-4-piperidinyl]methyl 8-amino-7-chloro-1,4-benzodioxan-5-carboxylate (E2)

4-Piperidinylmethyl 8-amino-7-chloro-1,4-benzodioxan-5-carboxylate (0.180 g, 0.55 mmol) was dissolved in acetone (10 ml) and treated with acrylonitrile (0.040 ml; 0.61 mmol). The solution was heated at reflux (18 hours), cooled and evaporated in vacuo to an orange gum. The gum was purified by flash silica-gel chromatography with CHCl$_3$→2% MeOH/CHCl$_3$ as eluant to yield the title compound as a colourless oil (0.035g; 17%) which was converted to the oxalate salt, mp 101°–103° C.

¹H NMR (250 MHz, CDCl₃) (free base) δ:7.47 (s, 1H), 4.47 (s, 2H), 4.40–4.30 (m, 4H), 4.10 (d, 2H), 2.90 (d, 2H), 2.70 (t, 2H), 2.50 (t, 2H), 2.17–2.03 (m, 2H), 1.85–1.70 (m, 3H), 1.50–1.30 (m, 2H).

EXAMPLE 3

[1-(3-Oxobutyl)-4-piperidinyl]methyl 8-amino-7-chloro-1, 4-benzodioxan-5-carboxylate (E3)

4-Piperidinylmethyl 8-amino-7-chloro-1,4-benzodioxan-5-carboxylate (0.100 g; 10.31 mmol) was dissolved in acetone (10 ml) and treated with triethylamine (0.043 ml; 0.31 mmol) and methyl vinyl ketone (0.026 ml; 0.34 mmol). The solution was heated at reflux (18 hours), cooled and evaporated in vacuo to a yellow gum. The gum was purified by flash silica-gel chromatography with CHCl₃ as eluant to yield the title compound as a colourless gum (0.050 g; 41%) which was converted to the oxalate salt.

m.p. 160° C. (Dec)

¹H NMR (250 MHz, CDCl₃) (Free base) δ: 7.47 (s, 1H), 4.47 (s, 2H), 4.40–1.30 (m, 4H), 4.10 (d, 2H), 2.90 (d, 2H), 2.65 (s, 4H), 2.17 (s, 3H), 2.00 (t, 2H), 1.85–1.70 (m, 2H), 1.47–1.25 (m, 3H)

EXAMPLE 4

[1-(2-Methylsulphonylaminoethyl)-4-piperidinyl]methyl 8-amino-7-chloro-1,4-benzodioxan-5-carboxylate (E4)

4-Piperidinylmethyl-8-amino-7-chloro-1,4-benzodioxan-5-carboxylate (0.144 g, 0.441 mmol) in acetonitrile (10ml) was treated with diisopropylethylamine (0.154 ml; 0.882 mmol), followed by N-(2-bromoethyl)methanesulphonamide (D2) (0.107 g, 0.529 mmol). The mixture was then heated to reflux under N₂. After 7 h, the reaction mixture was allowed to cool, and was then evaporated under reduced pressure, and the residue partitioned between CH₂Cl₂ and water. The aqueous layer was then extracted with CH₂Cl₂ (1X), and the combined organic layers were then dried (Na₂SO₄) and evaporated under reduced pressure to give a pale yellow oil. The oil was then purified by SiO₂ chromatography (5% MeOH/CHCl₃ as eluant) to give the title compound as a colourless oil (0.112 g, 57%), which was converted to its hydrochloride salt.

m.p. 248°–250° C.

¹HNMR (200 MHz, CDCl₃) (free base) δ: 7.50 (s, 1H), 4.50 (s, 2H), 4.35 (s, 4H), 4.12 (d, 2H), 3.22 (t, 2H), 3.00 (s, 3H), 2.90 (m, 2H), 2.55 (t, 2H), 2.08 (t, 2H), 1.90–1.60 (m, 3H), 1.50–1.22 (m, 3H)

EXAMPLE 5

[1(2-Acetylamino)ethyl]-4-piperidinyl]methyl 8-amino-7-chloro-1,4-benzodioxan-5-carboxylate (E5)

4-Piperidinylmethyl 8-amino-7-chloro-1,4,-benzodioxan-5-carboxylate (0.138 g, 0.423 mmol) was dissolved in CH₃CN (8 ml) and treated with N-(2-chloroethyl)acetamide (0.051 ml, 0.507 mmol), followed by diisopropylethylamine (0.147 ml, 0.846 mmol), and a catalytic amount of sodium iodide. The mixture was then heated to reflux with stirring. After 2 days, the reaction mixture was allowed to cool, before being evaporated under reduced pressure to give a pale yellow foam. The foam was then purified by silica-gel chromatography (CH₂Cl₂/10% MeOH) to give the title compound (0.025 g, 14%) as a colourless oil, which was converted to its oxalate salt m.p. 180°–182° C.

¹H NMR (270 MHz, CD₃SOCD₃) (oxalate salt) δ: 8.15 (s, 1H), 7.30 (s, 1H), 5.70 (s, 2H), 4.30 (s, 4H), 4.05 (d, 2H), 3.50–3.25 (m, 4H), 3.05–0.75 (m, 4H) 2.00–1.80 (m, 3H), 1.80 (s, 3H), 1.50 (m, 2H).

Description 1

4-Piperidinylmethyl 8-amino-7-chloro-(1,4-benzodioxan-5-carboxylate hydrochloride a) To a stirred solution of 8-amino-7-chloro-1,4-benzodioxan-5-carboxylic acid (prepared from the corresponding 7-H acid (prepared as in GB 1571278) by chlorination of the protected form) (1.10 g) in acetonitrile was added bis-carbonyldiimidazole (0.77 g). The reaction mixture was stirred at room temperature for 1.5 hours. The solvent was removed under reduced pressure to afford crude 8- amino-7-chloro-1,4-benzodioxan-5-imidazolide.

b) To a solution of N-tert-butoxycarbonyl-4-hydroxymethyl piperidine (0.25 g) in dry THF (10 ml) was added methyllithium (1.5M in diethylether; 0.78 ml) at 0° C. under a nitrogen atmosphere. Stirring was continued at ambient temperature for 10 min. 8-Amino-7-chloro-1,4-benzodioxan-5-imidazolide (0.33 g)in THF (10 ml) was added to the reaction mixture and stirring continued for 2 hours. The reaction mixture was cooled to 0° C. and water was added. The solvent was removed under reduced pressure and the residue partitioned between chloroform and water. The organic phase was washed with water (3×), dried (Na₂SO₄) filtered and concentrated in vacuo. Flash chromatography on silica using chloroform and ethanol as eluant gave the title compound (0.26 g).

¹H NMR 250 MHz (CDCl₃) δ: 7.47(s,1H), 4.49(s,2H), 4.08–4.22(m,4H), 2.64–2.80(m,2H), 1.84–2.01(m,1H), 1.70–1.83(m,2H), 1.46(s,9H), 1.18–1.38(m,2H)

c) HCl(g) was bubbled into a cooled solution of 8-amino-7-chloro-(N-tert-butoxycarbonyl-4-piperidylmethyl)-1,4-benzodioxan-5-carboxylate (0.26 g) in dioxan (50 ml) for 25 min. The solvent was concentrated in vacuo and the residue triturated with Et₂O to afford pure title compound (D1) (0.12 g).

mp 249°–251° C.

¹H NMR 250 MHz (DMSO) δ: 8.99–9.10(m,1H), 8.59–8.78(m,1H), 7.29(s, 1H), 5.73(s,2H), 4.25–4.34(s,4H), 4.03(d,2H), 3.20–3.42(m,2H), 2.75–2.97(m,2H), 1.76–2.06(m,3H), 1.48–1.57(m,2H)

Description 2

N-(2-Bromoethyl)methanesulphonamide 2-Bromoethylamine hydrobromide (5.10 g; 0.025 mol) was dissolved in dichloromethane (200 ml) with stirring, and treated with triethylamine (6.96 ml, 0.050 mol). The mixture was then cooled in ice and methanesulphonyl chloride (1.96 ml, 0.025 mol) added slowly. The reaction mixture was then allowed to warm to room temperature. After 16 h, the reaction mixture was washed with water (IX) and 5M HCl (IX), dried (Na₂SO₄), and evaporated under reduced pressure to give the title compound (D2) as a colourless oil that crystallised on standing to give a white solid (3.50 g, 69%).

¹HNMR (250 MHz, CDCl₃), δ: 4.92 (s, 1H), 3.62–3.48 (m, 4H), 3.05 (s, 3H).

5-HT₄ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% CO₂ in O₂ and maintained at 37° C. In all experiments, the Krebs solution also contains methiothepin $10^{-7}$M and granisetron $10^{-6}$M to block effects at 5-$HT_1$, 5-$HT_2$ and 5-$HT_3$ receptors.

After construction of a simple concentration-response curve with 5-HT, using 30s contact times and a 15 min dosing cycle, a concentration of 5-HT is selected so as to obtain a contraction of the muscle approximately 40–70% maximum($10^{-9}$M approx). The tissue is then alternately dosed every 15min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-$HT_4$ receptor antagonist are then added to the bathing solution. The effects of this compound are then determined as a percentage reduction of the contractions evoked by 5-HT or by DMPP. From this data, $pIC_{50}$ values are determined, being defined as the −log concentration of antagonist which reduces the contraction by 50%. A compound which reduces the response to 5-HT but not to DMPP is believed to act as a 5-$HT_4$ receptor antagonist.

The compounds generally had a $pIC_{50}$ of at least 8 and E1 had a $pIC_{50}$ of 10.2.

2) Piglet Atria

Compounds are tested in the piglet spontaneous beating screen (Naunyn-Schmiedeberg's Arch. Pharmacol 342, 619–622) and $pK_B$ ($-\log_{10}K_B$) values determined.

3) Rat oesophagus

Rat oesophageal tunica muscularis mucosae is set up according to Baxter et. al. Naunyn-Schmiedeberg's Arch. Pharmacol., 343, 439–446 (1991). The inner smooth muscle tube of the muscularis mucosae is isolated and mounted for isometric tension recording in oxygenated (95% $O_2$/5% $CO_2$) Tyrodes solution at 37° C. All experiments are performed in pargyline pre-treated preparations (100 μM for 15 min followed by washout) and in the presence of cocaine (30 μM). Relaxant responses to 5-HT are obtained after pre-contracting the oesophagus tissue with carbachol (3 μM).

4) 5-HT-induced motility in dog gastric pouch

Compounds are tested for inhibition in the in vivo method described in "Stimulation of canine motility by BRL 24924, a new gastric prokinetic agent", Bermudez et al, J. Gastrointestinal Motility, 1990, 2(4), 281–286.

We claim:

1. A compound of formula (I), or a pharmaceutically acceptable salt thereof:

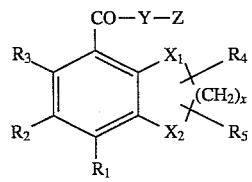

in which $X_1$—$(CH_2)_x$—$X_2$ forms a 5–7 membered ring wherein:

$X_1$ is O or S;

$X_2$ is O, S, NR or NRCO wherein R is hydrogen or $C_{1-6}$ alkyl;

x is 1, 2 or 3;

$R_1$ is hydrogen, amino, halo, $C_{1-6}$ alkyl, hydroxy or $C_{1-6}$ alkoxy;

$R_2$ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkyl, $C_{1-6}$ alkoxy or amino;

$R_4$ and $R_5$ are independently hydrogen or $C_{1-6}$ alkyl;

Y is O;

Z is of sub-formula (a):

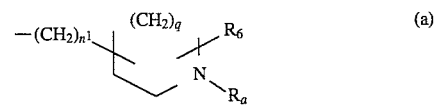

wherein

—$(CH_2)_{n^1}$ is attached at carbon: and $n^1$ is 0, 1, 2, 3 or 4;

q is 0, 1, 2 or 3;

$R_a$ is $(CH_2)_{n^2}$-$R_7$ wherein $n^2$ is 2 or 3 and $R_7$ is selected from cyano, hydroxyl, $C_{1-6}$ alkoxy, phenoxy, $C(O)C_{1-6}$ alkyl, $COC_6H_5$, —$CONR_8R_9$, $NR_8COR_9$, $SO_2NR_8R_9$ or $NR_8SO_2R_9$ wherein $R_8$ and $R_9$ are hydrogen or $C_{1-6}$ alkyl; and $R_6$ is hydrogen or $C_{1-6}$ alkyl;

having 5-$HT_4$ receptor antagonist activity.

2. A compound according to claim 1 wherein $X_1$—$(CH_2)_x$—$X_2$ moiety is O—$(CH_2)_2$—O, O—$(CH_2)_3$—O, O—$CH_2$—O, O—$(CH_2)_2$—NR, O—$(CH_2)_2$—S or O—$CH_2$—CONR, wherein R is as defined in claim 1 and any of the methylene linkages are optionally mono- or di-substituted by $C_{1-6}$ alkyl groups.

3. A compound according to claim 2 wherein $X_1$—$(CH_2)_2$—$X_2$ is O—$(CH_2)_2$—O.

4. A compound according to claim 1, wherein $R_1$ is hydrogen or amino, $R_2$ is hydrogen or halo, and $R_3$ is hydrogen or halo.

5. A compound according to claim 1, wherein $R_a$ is $(CH_2)_3OH$, $(CH_2)_2CN$, $(CH_2)_2COCH_3$, $(CH_2)_2NHSO_2CH_3$, or $(CH_2)_2NHCOCH_3$.

6. A compound according to any one of claim 1 wherein $n^1$ is 1 and the azacycle is attached at a 4-position carbon atom, when q is 2.

7. A compound according to claim 6 wherein Z is N-substituted 4-piperidylmethyl.

8. A compound according to claim 2 wherein $R_1$ is hydrogen or amino, $R_2$ is hydrogen or halo, and $R_3$ is hydrogen or halo.

9. A compound according to claim 8 wherein $R_a$ is $(CH_2)_3OH$, $(CH_2)_2CN$, $(CH_2)_2COCH_3$, $(CH_2)_2NHSO_2CH_3$ OR $(CH_2)_2NHCOCH_3$.

10. A compound according to claim 9 wherein $n^1$ is 1 and the azacycle is attached at a 4-position carbon atom, when 1 is 2.

11. A compound which is:

[1-(3-hydroxypropyl)-4-piperidinyl]methyl 8-amino-7-chloro-1,4-benzodioxan-5-carboxylate;

[1-(2-cyanoethyl)-4-piperidinyl]methyl 8-amino-7-chloro-1,4-benzodioxan-5-carboxylate;

[1-(3-oxobutyl)-4-piperidinyl]methyl 8-amino-7-chloro-1,4-benzodioxan-5-carboxylate;

[1-(2-methylsulphonylaminoethyl)-4-piperidinyl]methyl 8-amino-7-chloro-1,4-benzodioxan-5-carboxylate;

[1-(2-acetylaminoethyl)-4-piperidinyl]methyl 8-amino-7-chloro-1,4-benzodioxan-5-carboxylate; or a pharmaceutically acceptable salt thereof.

12. A pharmaceutical composition comprising a compound according to any one of claims 1 to 11, and a pharmaceutically acceptable carrier.

13. A method of treating IBS which comprises administering a compound according to claim 1.

14. A method of treating urinary incontinence which comprises administering a compound according to claim 1.

15. A method of treating nausea and emesis which comprises administering a compound according to claim 1.

16. A method of treating migraine which comprises administering a compound according to claim 1.

17. A method of treating anxiety which comprises administering a compound according to claim 1.

18. A method of treating schizophrenia which comprises administering a compound according to claim 1.

19. A method of treating atrial fibrillation and stroke which comprises administering a compound according to claim 1.

* * * * *